US006506262B2

(12) United States Patent
Strout et al.

(10) Patent No.: US 6,506,262 B2
(45) Date of Patent: Jan. 14, 2003

(54) CLEANSER

(75) Inventors: Kelly Michael Strout, Roswell, GA (US); Peter Maddern, North Wales (GB)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 43 days.

(21) Appl. No.: 09/726,091

(22) Filed: Nov. 29, 2000

(65) Prior Publication Data

US 2002/0132750 A1 Sep. 19, 2002

Related U.S. Application Data

(62) Division of application No. 09/057,167, filed on Apr. 8, 1998, now abandoned.

(51) Int. Cl.[7] .......................... B08B 3/04; A61K 9/133; C11D 7/40; C11D 17/08

(52) U.S. Cl. ...................... 134/40; 134/25.2; 134/25.3; 134/38; 134/39; 134/42; 510/130; 510/138; 510/174; 510/238; 510/239; 510/240; 510/365; 510/441; 510/468; 424/452; 424/455; 424/450; 424/420; 424/490

(58) Field of Search .............................. 134/25.2, 25.3, 134/38, 39, 40, 42; 510/130, 138, 174, 238, 239, 240, 365, 441, 468; 424/452, 455, 450, 420, 490

(56) References Cited

U.S. PATENT DOCUMENTS

| | | | | |
|---|---|---|---|---|
| 4,853,228 A | 8/1989 | Wallach et al. | 424/450 |
| 4,855,090 A | 8/1989 | Wallach | 264/4.1 |
| 4,895,452 A | 1/1990 | Yiournas et al. | 366/173 |
| 4,911,928 A | 3/1990 | Wallach | 424/450 |
| 4,917,951 A | 4/1990 | Wallach | 428/402.2 |
| 4,942,038 A | 7/1990 | Wallach | 424/450 |
| 5,000,960 A | 3/1991 | Wallach | 424/450 |
| 5,013,497 A | 5/1991 | Yiournas et al. | 264/4.1 |

(List continued on next page.)

FOREIGN PATENT DOCUMENTS

| | | | |
|---|---|---|---|
| FR | 2490504 | 3/1982 | B01F/17/00 |
| WO | WO 91/00084 | 1/1991 | A61F/9/127 |
| WO | WO 91/04731 | 4/1991 | A41K/9/127 |
| WO | WO 92/06676 | 4/1992 | A61K/9/127 |

OTHER PUBLICATIONS

"Cleaning & Conditioning Now All–In–One", Kimberly Clark Brochure, pp. 1–2, 1997. This product was test marketed in Oct. 1993.

Dr. Norman D. Weiner, *Lipsomes Potential For Commercial Application*, presented at the Emulsion–Suspension Technology course, Oct. 20–23, 1997, New Brunswick, NJ, given by The Institute for Applied Pharmaceutical Services.

"Technical Description of Novasome® Lipid Vesicle Technology", Donald F.H. Wallach, M.D., Revision Nov. 1993.

*Primary Examiner*—Yogendra N. Gupta
*Assistant Examiner*—Brian P. Mruk
(74) *Attorney, Agent, or Firm*—Nelson Mullins Riley & Scarborough

(57) ABSTRACT

The present invention may include a cleanser having a liposome and greater than about 40 weight percent of a solvent. The liposome may be loaded with the solvent more than about 7 days after the manufacture of the liposome. The solvent may be an isoprenoid or ester solvent. Furthermore, the solvent may be d-limonene or a dibasic ester. In addition, the liposome may be selected from the group consisting of large unilamellar vesicles, multilamellar vesicles, paucilamellar vesicles, and small unilamellar vesicles. Desirably, the liposome is a paucilamellar vesicle. Desirably, the cleanser may have a solvent weight percent greater than about 60. More desirably, the cleanser may have a weight percent of solvent greater than about 80. Moreover, the solvent is about a 1:1 weight ratio of d-limonene and dibasic ester.

10 Claims, 4 Drawing Sheets

U.S. PATENT DOCUMENTS 5,019,174 A * 5/1991 Wallach .......................... 134/40
5,019,392 A 5/1991 Wallach .......................... 424/420
5,023,086 A 6/1991 Wallach .......................... 424/450
5,032,457 A 7/1991 Wallach .......................... 428/402.2
5,104,736 A 4/1992 Wallach .......................... 428/402.2
5,147,723 A 9/1992 Wallach .......................... 428/402.2
5,160,669 A 11/1992 Wallach et al. ............... 264/4.3
5,164,191 A 11/1992 Tabibi et al. ................. 424/450
5,213,805 A 5/1993 Wallach et al. ............... 424/450
5,219,538 A 6/1993 Henderson et al. .......... 428/402.2
5,229,104 A 7/1993 Sottery et al. ................ 424/59
5,234,767 A 8/1993 Wallach .......................... 428/402.2
5,256,422 A 10/1993 Albert et al. ................ 424/450
5,260,065 A 11/1993 Mathur et al. ............... 424/450
5,264,553 A 11/1993 Hou ................................ 528/502
5,376,183 A 12/1994 Gatt et al. .................... 134/40
5,401,413 A 3/1995 Gatt et al. .................... 210/610
5,405,615 A 4/1995 Mathur ........................... 424/450
5,439,967 A 8/1995 Mathur ........................... 424/450
5,441,666 A 8/1995 Dotolo ............................ 252/170
5,474,848 A 12/1995 Wallach ......................... 428/402.2
5,490,985 A 2/1996 Wallach et al. ............... 424/450
5,510,112 A 4/1996 Gatt et al. .................... 424/450
5,542,987 A 8/1996 Gatt et al. .................... 134/39
5,554,730 A 9/1996 Woiszwillo et al. .......... 530/410
5,561,062 A 10/1996 Varanelli et al. ............ 435/238
5,593,508 A 1/1997 Gatt et al. .................... 134/40
5,686,113 A 11/1997 Speaker et al. .............. 424/490
5,700,679 A 12/1997 Wright ............................ 435/238
5,710,296 A 1/1998 Foland et al. ................ 554/167
5,728,662 A 3/1998 Vlasblom ....................... 510/130

* cited by examiner

CLEANSER

This is a divisional application of prior application Ser. No. 09/057,167 filed Apr. 8, 1998 abandoned, entitled "A Cleanser", of which this application claims parent benefit under 35 U.S.C. §120.

FIELD OF THE INVENTION

This invention generally relates to the field of cleansers, cleansing products, or processes of making cleansers.

BACKGROUND

Liposomes or lipid vesicles are closed bilayer structures. The bilayer structure includes two membranes. Each membrane has a polar end and a nonpolar end. The membranes in the bilayer may either have their polar ends or nonpolar ends in an abutting relation. There are many uses for these structures, such as adjuvants and carriers for the transportation of encapsulated drugs or biologically-active substances.

Often, a lipid vesicle is classified into three groups by size and structure: large unilamellar vesicle (hereinafter may be referred to as "LUV"), small unilamellar vesicle (hereinafter may be referred to as "SUV"), and multilamellar vesicle (hereinafter may be referred to as "MLV"). LUV may have a diameter greater than about 1 micron and may be formed of a lipid bilayer surrounding a large, unstructured aqueous phase. SUV may be similar in structure to the LUV except their diameters may be less than about 0.2 micron. A MLV may have an onion-like structure having a series of substantially spherical shells formed of lipid bilayers interspersed with aqueous layers. LUV, SUV, and MLV structures may be manufactured by various mechanisms, including those described in "LIPOSOMES—Potential for Commercial Application", by Dr. Norman D. Weiner, presented at the Emulsion-Suspension Technology Conference, Oct. 20–23, 1997, at New Brunswick, N.J.

A fourth type of lipid vesicle, which may be particularly well suited for transport of either lipids or aqueous materials, is a paucilamellar vesicle (hereinafter may be referred to as "PLV"). This type of vesicle may have an external structure of about two to about eight peripheral lipid bilayers with a large, unstructured aqueous center. Liquid droplets, such as oil, may be suspended in the center, leading to very high uptake of non-aqueous or lipophilic materials. The paucilamellar vesicle may range from about 2 to about 15 micron in diameter. Methods of making PLV are described in U.S. Pat. No. 4,911,928 to Wallach, issued Mar. 27, 1990.

Besides being used as medical delivery devices, liposomes, particularly PLVs, may be used as cleansers. These cleansers may be used to remove oil and/or dirt from surfaces, such as skin. Desirably, these liposomes encapsulate a non-aqueous solution and are applied to a surface. Agitation, such as rubbing ones hands, may break the liposomes freeing the non-aqueous solution. Afterwards, the liposomes may reform encapsulating the oil and dirt. The freed non-aqueous solution may aid in removing the liposomes from the surface.

Unfortunately, these cleansers suffer several disadvantages. Although liposomes may be used as cleansers for various organic contaminates, they may not be adequate for some contaminates, such as those present in the paint and printing industry. Furthermore, liposomes may benefit the skin by replacing natural oils lost during the cleansing process. Removing the liposomes after cleansing probably deprives the skin of this benefit. Also, the conventional wisdom is that no more than 40 weight percent cleansing solvent may be loaded into the premade PLVs. This solvent loading ceiling may limit the amount of added solvent to the liposomes, thereby impeding subsequent cleaning. Moreover, it is believed that as the PLV ages, the amount of solvent loaded into the PLV will be reduced. Currently, it is recommended loading PLVs with solvent within a week of the PLVs manufacture date, or ideally, during the PLV manufacturing process. This time constraint may limit manufacturing flexibility, and also result in waste of materials.

Accordingly, a liposome cleanser that increases use and manufacture versatility, acts as skin moisturizer, and improves manufacturing efficiencies, will improve over conventional liposome cleansers.

DEFINITIONS

As used herein, the term "include" refers to a part or parts of a whole, but does not exclude other parts. The term "include" may have the same meaning and may be interchanged with the terms "comprise" and "have".

As used herein, the term "cleanser" refers to a substance, such as a liquid, suspension, or powder, used to free foreign or extraneous matter. Cleanser examples include soaps, detergents, solvents, and liposomal cleansers. A liposomal cleanser may include a liposome having an aqueous center that entrains a solvent.

As used herein, the term "carrier" refers to a liquid substance that supports another substance. In addition, a carrier may have other properties, such as cleaning properties, and particularly, may act as a surfactant.

As used herein, the term "cleansing product" refers to a product having a cleanser and a carrier.

As used herein, the term "liposome" means a closed lamellar vesicle that forms in aqueous suspensions of various lipids or lipid mixtures. The term "liposome" may have the same meaning and may be interchanged with the term "lipid vesicle". Liposome examples include large unilamellar vesicles, multilamellar vesicles, paucilamellar vesicles, small unilamellar vesicles, reverse phase evaporation vesicles, French press vesicles, and ether injection vesicles. Products incorporating liposomes include adjuvants, drug carriers, and cleansers. The following references disclose methods and/or apparatuses for manufacturing liposomes: "LIPOSOMES—Potential for Commercial Application", by Dr. Norman D. Weiner, presented at the Emulsion-Suspension Technology Conference, Oct. 20–23, 1997, at New Brunswick, N.J.; U.S. Pat. No. 4,911,928 to Wallach, issued Mar. 27, 1990; U.S. Pat. No. 4,855,090 to Wallach, issued Aug. 8, 1989; and U.S. Pat. No. 4,895,452 to Yiournas et al., issued Jan. 23, 1990.

As used herein, the term "vesicle" means a small, thin-walled bladderlike cavity, typically filled with fluid.

As used herein, the term "manufactured" means to have made a material functional for its intended purpose. Manufactured does not mean any subsequent commercial steps, such as packaging or bottling.

As used herein, the term "isoprenoid" means substances that include isoprene units of the chemical formula $C_5H_8$. Isoprenoids include terpenes, sesquiterpenes, diterpenes, and triterpenes. Isoprenoids may be extracted from plants such as cloves, roses, lavender, citronella, eucalyptus, peppermint, camphor, sandalwood, cedar, and turpentine.

As used herein, the term "ester" refers to a substance formed by the bonding of an alcohol and an organic acid.

Ester examples include animal fats, such as stearic acid, and fragrances, such as isopentyl acetate or octyl acetate.

As used herein, the term "dibasic ester" refers to an ester containing two hydrogens that may be replaced by a monovalent metal or radical. Examples of dibasic esters include dimethyl glutarate, dimethyl adipate, and dimethyl succinate.

As used herein, the term "solvent" refers to a material that dissolves another substance while not changing its physical state. The solvent does not have to be the majority component of the resultant solution. Examples of solvents include synthetic and natural hydrocarbons. Synthetic and natural hydrocarbons may include dibasic esters, terpenes, mixtures of isoprenoid and mineral oil substances, naphthas, glycol ethers, parrafinic and isoparrafinic hydrocarbons, aromatic hydrocarbons, petroleum distillates, vegetable oils, animal oils, organic halides, halogenated solvents, and alcohols. Terpenes may include d-limonene and the dibasic esters may include dimethyl glutarate, dimethyl adipate, and dimethyl succinate.

As used herein, the term "large unilamellar vesicle" refers to a lipid bilayer surrounding a large, unstructured aqueous phase and having a diameter greater than about 1 micron. The term "large unilamellar vesicle" may be abbreviated as "LUV" and a plurality of large unilamellar vesicles may be abbreviated as "LUVs". FIG. 1 is a schematic illustration of an exemplary LUV 10. The LUV 10 may include an amorphous center 20 and a bilayer 30.

As used herein, the term "small unilamellar vesicle" refers to a lipid bilayer surrounding a unstructured aqueous phase and having a diameter less than about 0.2 micron. The term "small unilamellar vesicle" may be abbreviated as "SUV" and a plurality of small unilamellar vesicles may be abbreviated as "SUVs". FIG. 2 is a schematic illustration of an exemplary SUV 100. The SUV 100 may include an amorphous center 120 and a bilayer 130.

As used herein, the term "multilamellar vesicle" refers to an onion-like structure having a series of substantially spherical shells formed of lipid bilayers interspersed with aqueous layers and a diameter from about 0.05 to about 10.0 micron. The term "multilamellar vesicle" may be abbreviated as "MLV" and a plurality of multilamellar vesicles may be abbreviated as "MLVs". FIG. 3 is a schematic illustration of an exemplary MLV 200. The MLV 200 may include an amorphous center 220 and eight bilayers 230–237.

As used herein, the term "paucilamellar vesicle" refers to an external structure having about two to about eight peripheral lipid bilayers with a large, unstructured aqueous center and a diameter from about 2 to about 15 micron. The term "paucilamellar vesicle" may be abbreviated as "PLV" and a plurality of paucilamellar vesicles may be abbreviated as "PLVs". FIG. 4 is a schematic illustration of an exemplary PLV 300. The PLV 300 may include an amorphous center 320 and three bilayers 330–332. Generally, PLVs have a larger center than MLVs, permitting PLVs to encapsulate more drugs or solvents.

As used herein, the term "means for encapsulating" refers to substance encapsulating a solvent. Means for encapsulating examples include liposomes and gelatin beads.

As used herein, the term "weight percent" refers to the ratio of the weight of a particular component to the total weight of the whole item multiplied by 100. As an example, 40 grams of a solvent loaded into 60 grams of a liposome may be expressed as 40 weight percent solvent.

SUMMARY OF THE INVENTION

The problems and needs described above are addressed by the present invention, which provides a cleanser including a liposome and greater than about 40 weight percent of a solvent. The liposome may be loaded with the solvent more than about 7 days after the manufacture of the liposome. The solvent may be an isoprenoid or ester solvent. Furthermore, the solvent may be d-limonene or a dibasic ester. In addition, the liposome may be selected from the group consisting of large unilamellar vesicles, multilamellar vesicles, paucilamellar vesicles, and small unilamellar vesicles. Desirably, the liposome is a paucilamellar vesicle. Desirably, the cleanser may have a solvent weight percent greater than about 60. More desirably, the cleanser may have a weight percent of solvent greater than about 80. Moreover, the solvent may be about a 1:1 weight ratio of d-limonene and dibasic ester.

In addition, the present invention includes a process of making a cleanser. The process may include the steps of providing a liposome, providing a solvent, and loading the liposome so the liposome contains greater than about 40 weight percent of the solvent. The solvent may be an isoprenoid or ester solvent. Moreover, the solvent may be d-limonene or a dibasic ester. Furthermore, the liposome may be selected from the group consisting of large unilamellar vesicles, multilamellar vesicles, paucilamellar vesicles, and small unilamellar vesicles. Desirably, the liposome is a paucilamellar vesicle. Desirably, the solvent weight percent may be greater than about 60. More desirably, the solvent weight percent may be greater than about 80.

Moreover, the present invention includes another process for making a cleanser. The process may include the steps of providing a liposome, providing a solvent, and loading the liposome with the solvent. The loading may be carried out more than about 7 days after the manufacture of the liposome. In addition, the loading may be carried out more than about 21 days after the manufacture of the liposome. Likewise, the loading may be carried out more than about 60 days after the manufacture of the liposome. Similarly, the loading may be carried out more than about 90 days after the manufacture of the liposome.

Furthermore, the present invention includes a cleanser having a means for encapsulating and greater than about 40 weight percent of a solvent. The means for encapsulating may be a liposome. Desirably, the liposome is selected from the group consisting of large unilamellar vesicles, multilamellar vesicles, paucilamellar vesicles, and small unilamellar vesicles. The solvent may be d-limonene or a dibasic ester.

Also, the present invention includes a cleanser having a paucilamellar vesicle and greater than about 40 weight percent of a dibasic ester solvent. The paucilamellar vesicle may be loaded with the solvent more than about 90 days after the manufacture of the paucilamellar vesicle.

Moreover, the present invention includes a cleanser made by including a liposome and greater than about 40 weight percent of a solvent. The liposome may be loaded with the solvent more than about 7 days after the manufacture of the liposome.

Furthermore, the present invention includes a cleansing product including a cleanser having a liposome and a carrier. The liposome may be loaded with greater than about 40 weight percent of a solvent more than about 7 days after the manufacture of the liposome.

Likewise, the present invention includes a cleanser including a means for encapsulating and a solvent where the cleanser has a cleaning percent for oil based printers ink greater than about 50 percent.

DETAILED DESCRIPTION OF THE PREFERRED EMBODIMENT(S)

Figure 1:
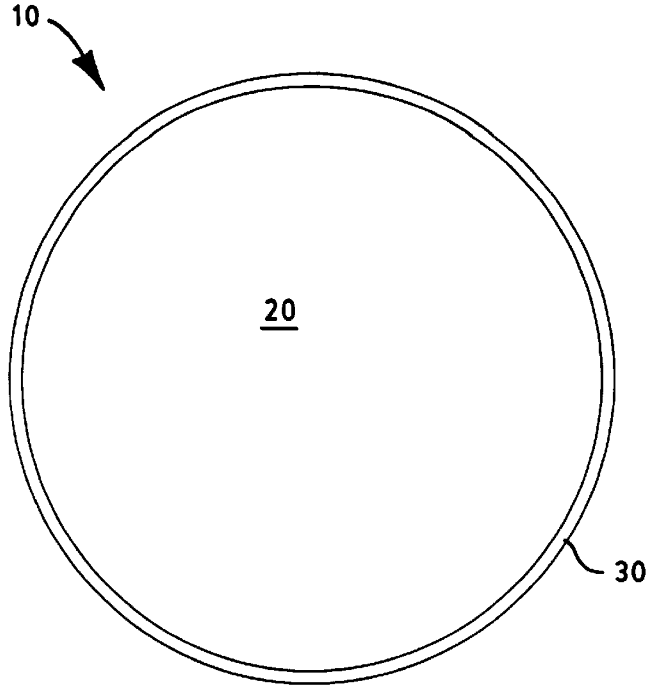
FIG. 1 is a schematic illustration, not necessarily to scale, of an exemplary LUV.
Figure 2:
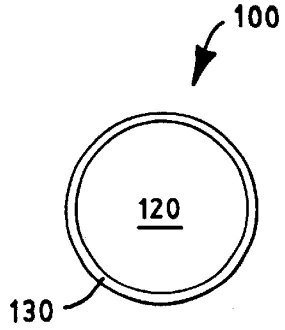
FIG. 2 is a schematic illustration, not necessarily to scale, of an exemplary SUV.
Figure 3:
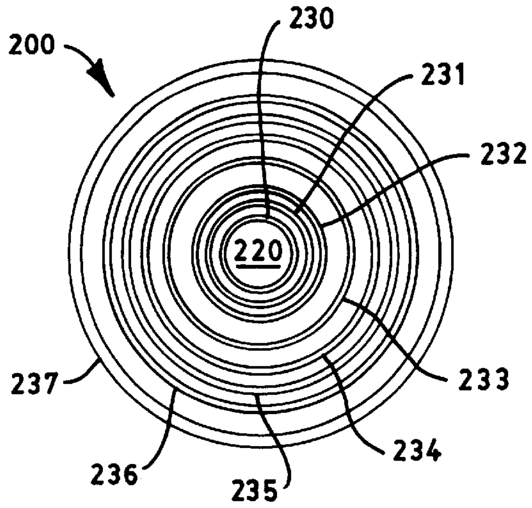
FIG. 3 is a schematic illustration, not necessarily to scale, of an exemplary MLV.
Figure 4:
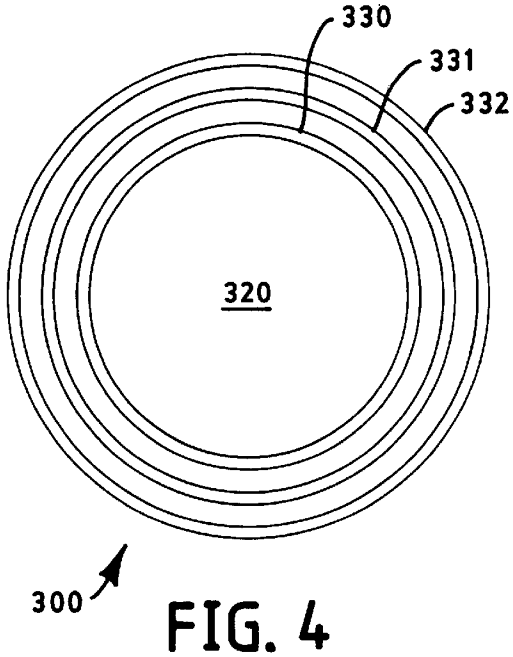
FIG. 4 is a schematic illustration, not necessarily to scale, of an exemplary PLV.

The cleanser of the present invention may include a means for encapsulating and a solvent. Means for encapsulating may include liposomes and gelatin beads. The liposomes may include LUV, SUV, MLV, and PLV. Desirably, the liposome is a MLV or PLV, and more desirably a PLV. The LUV, SUV, and MLV may be manufactured by a variety of methods recognized by those skilled in art, such as methods disclosed in "LIPOSOMES—Potential for Commercial Application", by Dr. Norman D. Weiner, presented at the Emulsion-Suspension Technology Conference, Oct. 20–23, 1997, at New Brunswick, N.J., which is hereby incorporated by reference. The following three patents, which are hereby incorporated by reference, describe methods and/or apparatuses for making MLV and/or PLV: U.S. Pat. No. 4,911,928 to Wallach, issued Mar. 27, 1990, discloses a method of making paucilamellar lipid vesicles; U.S. Pat. No. 4,855,090 to Wallach, issued Aug. 8, 1989, describes a method for preparing multilayered liposomes suitable for incorporating aqueous solutions of hydrophilic materials; and U.S. Pat. No. 4,895,452 to Yiournas et al., issued Jan. 23, 1990, discloses an apparatus for the production of multilamellar and paucilamellar lipid vesicles. Liposomes, which have polar and nonpolar structures, may help dissolve water-insoluble, nonaqueous solvents in water.

Examples of solvents that may be used in the present invention include synthetic and natural hydrocarbons. Synthetic and natural hydrocarbons may include dibasic esters, terpenes, mixtures of isoprenoid and mineral oil substances, naphthas, glycol ethers, parrafinic and isoparrafinic hydrocarbons, aromatic hydrocarbons, petroleum distillates, vegetable oils, animal oils, organic halides, halogenated solvents, and alcohols. Terpenes may include d-limonene and the dibasic esters may include dimethyl glutarate, dimethyl adipate, and dimethyl succinate. Water-insoluble, nonaqueous solvents include d-limonene and dibasic esters.

Various PLVs and solvent weight percents may be used with the present invention. The PLVs weight percent may be about 95, and correspondingly, the solvent weight percent may be about 5. Furthermore, the PLVs weight percent may be about 80, and correspondingly, the solvent weight percent may be about 20. In addition, the PLVs weight percent may be about 70, and correspondingly, the solvent weight percent may be about 30. Still further, the PLVs weight percent may be about 60, and correspondingly, the solvent weight percent may be about 40. Desirably, the PLVs weight percent may be about 40, and correspondingly, the solvent weight percent may be about 60. More desirably, the PLVs weight percent may be about 20, and correspondingly, the solvent weight percent may be about 80.

Although the following examples utilize PLVs, it should be understood that other means for encapsulating, such as LUV, MLV, and SUV, may be used, including various combinations thereof. Furthermore, the solvent may be homogeneous solvent or mixtures of a plurality of solvents.

Loading Examples

The following loading examples utilized PLVs sold under the trade designation NOVASOME™ paucilamellar liposomal dispersions manufactured by Micro Vesicular Systems Inc. of Nashua, N.H. The NOVASOME™ paucilamellar liposomal dispersions used in the following examples were manufactured more than about 90 days prior to solvent loading.

Also, the following loading examples utilized a dibasic ester sold under the trade designation SANTOSOL DME-1™ manufactured by Monsanto, Inc., of 8000 North Lindbergh Boulevard, St. Louis, Mo. 63167. Furthermore, the following loading examples utilized a d-limonene sold under the trade name REDD SPECIAL ORANGE TERPENES™ manufactured by Tastemaker of 4705 U.S. Highway 92 East, Lakeland, Fla. 33801. D-limonene is a turpentine oil derivative, which may be used as a hand cleaner.

Further, the following examples utilized a LIGHTNIN™ bench top mixer manufactured by LIGHTNIN/General Equipment Division of 16490 Chillicothe Road, Chagrin Falls, Ohio. 44023-4398. The LIGHTNIN™ bench top mixer was fitted with a A-310 impeller. The PLVs and solvent were mixed from about 20 to about 70 minutes, or until a homogenous mixture was obtained. The impeller rotated at about 650 revolutions per minute. The mixture was heated from about 40 to about 98 degrees Celsius (hereinafter may be abbreviated "° C."), although in at least one example no heating was required, such as with the dibasic ester solvent. Loading the PLVs with solvent may result in some solvent remaining outside the PLVs. This unloaded solvent may form a solution with the PLVs.

Examples 1–4 illustrate loading PLVs to contain about 60 weight percent solvent.

EXAMPLE 1

PLVs in an amount of 411.15 grams were placed in the mixer and heated to 60° C. Next, d-limonene in an amount of 602.11 grams was added and mixed for 20 minutes at 60° C. Afterwards, the mixture was mixed for another 20 minutes with the heat turned off. After mixing, the finished cleanser was removed from the mixer.

EXAMPLE 2

PLVs in an amount of 404.02 grams were placed in the mixer and heated to 60° C. Next, a dibasic ester in an amount of 604.04 grams was added and mixed for 20 minutes at 60° C. Afterwards, the mixture was mixed for another 20 minutes with the heat turned off. After mixing, the cleanser was removed from the mixer.

After 24 hours, some of the dibasic ester was not loaded into the PLVs. Remixing for 30 minutes resulted in the unloaded dibasic ester loading into the PLVs.

EXAMPLE 3

PLVs in an amount of 120.00 grams were placed in the mixer and heated to 70° C. Next, d-limonene in an amount of 180.04 grams was added and mixed for 20 minutes at 80° C. Afterwards, the mixture was brought to room temperature and reheated to 40° C. for 30 minutes. After cooling, the finished cleanser was removed from the mixer.

EXAMPLE 4

PLVs in an amount of 402.10 grams were placed in the mixer and heated to 60° C. Next, d-limonene in an amount of 300.02 grams and a dibasic ester in an amount of 300.08 grams was added and mixed for 20 minutes at 60° C. Afterwards, the mixture was mixed for another 30 minutes with the heat turned off. After mixing, the finished cleanser was removed from the mixer.

Examples 5–7 illustrate loading PLVs to contain about 40 weight percent solvent.

EXAMPLE 5

PLVs in an amount of 180.35 grams were placed in the mixer and heated to 70° C. Next, d-limonene in an amount of 120.00 grams was added and mixed for 20 minutes at 70° C. Afterwards, the mixture was brought to room temperature and reheated to 40° C. for 30 minutes. After cooling, the finished cleanser was removed from the mixer.

EXAMPLE 6

PLVs in an amount of 450.02 grams were placed in the mixer and heated to 70° C. Next, d-limonene in an amount of 300.05 grams was added and mixed for 30 minutes at 70° C. Afterwards, the finished cleanser was removed from the mixer.

EXAMPLE 7

PLVs in an amount of 450.02 grams and a dibasic ester in an amount of 299.99 grams were placed in the mixer and mixed for 30 minutes at room temperature. Afterwards, the finished cleanser was removed from the mixer.

Example 8 illustrates loading PLVs to contain about 30 weight percent solvent.

EXAMPLE 8

PLVs in an amount of 349.99 grams were placed in the mixer and heated to 80° C. Next, d-limonene in an amount of 150.00 grams was added and mixed for 30 minutes. Afterwards, the finished cleanser was removed from the mixer.

Example 9 illustrates loading PLVs to contain about 20 weight percent solvent.

EXAMPLE 9

PLVs in an amount of 320.47 grams were placed in the mixer and heated to 98° C. Next, d-limonene in an amount of 80.63 grams was added and the heat removed. Mixing was continued until the mixture reached room temperature. Afterwards, the mixture was reheated to 40° C. for 30 mixtures. After cooling, the finished cleanser was removed from the mixer.

Example 10 is a prophetic example of loading PLVs with about 40 weight percent solvent.

EXAMPLE 10

PLVs in an amount of 600.02 grams would be placed in the mixer and heated to 70° C. Next, UNOCAL KMS 92-5™ solvent manufactured by United Oil of 14141 Southwest Freeway, Sugar Land, Tex. 77478 in an amount of 400.02 grams would be slowly added. The mixture would be cooled to 50° C. with the addition of UNOCAL™ and returned to 70° C., and then the heat would be removed and the mixture mixed for 30 minutes. Afterwards, the mixture would be reheated to 80° C. and mixed for 30 minutes. After cooling, the finished cleanser would be removed from the mixer.

CLEANSER PRODUCT EXAMPLE

The cleansers of the present invention may be mixed with a carrier, such as an EMULSION BLEND™ carrier or an INDUSTRIAL BLEND™ carrier manufactured by Rhone-Poulenc of CN 7500, Prospect Plains Road, Cranbury, N.J. 08512. It should be understood that the carrier may also act as a surfactant, and thus, the EMULSION BLEND™ carrier or the INDUSTRIAL BLEND™ carrier may be referred to, respectively, as an EMULSION BLEND™ surfactant or an INDUSTRIAL BLEND™ surfactant. The carriers help maintain the PLVs in solution with any unloaded solvent. Desirably, a relatively inexpensive carrier, such as the EMULSION BLEND™ surfactant or the INDUSTRIAL BLEND™ surfactant, is used with the cleanser to reduce manufacturing costs.

The following example, Example 11, is of a method of making a cleanser and a carrier product (hereinafter may be referred to as a "cleansing product"). In particular, the cleanser may be NOVASOME™ PLVs loaded with about 40 or about 60 weight percent solvent and the carrier may be a mixture of the EMULSION BLEND™ carrier and an INDUSTRIAL BLEND™ carrier.

EXAMPLE 11

The cleansing product includes two parts. The first part includes NOVASOME™ PLVs loaded with 40 weight percent d-limonene, a blended surfactant, such as EMULSION BLEND™ surfactant, d-limonene, and an expanded pumice including sodium potassium aluminum silicate, such as RYOLEX 30-1™ pumice manufactured by Silbrico Corporation of 6300 River Road, Hodgkins, Ill. 60525. The second part includes non-chlorinated water, a blended surfactant, such as INDUSTRIAL BLEND™ surfactant, and a DMDM hydantion, methylparaben, and propyl paraben preservative, such as PARAGON™ manufactured by The McIntyre Group of 24601 Governors Highway, University Park, Ill. 60466.

The first part was made by placing NOVASOME™ PLVs loaded with 40 weight percent d-limonene in an amount of 437.29 grams, an EMULSION BLEND™ surfactant in an amount of 184.12 grams, d-limonene in an amount of 29.11 grams, and RYOLEX 30-1™ in an amount of 19.38 grams, in the mixer at 1250 revolutions per minute and mixing for at least 30 minutes until consistent at about 57° C. to about 63° C.

The second part was made by placing non-chlorinated water in an amount of 146.32 grams, INDUSTRIAL BLEND™ surfactant in an amount of 182.73 grams, and PARAGON™ in an amount of 2.69 grams, in the mixer at 1250 revolutions per minute and mixing for at least 30 minutes until consistent at about 32° C. to about 38° C.

Afterwards, the heat was removed and the second part was blended into the first part for at least 30 minutes until consistent. After mixing, the cleansing product may be used to clean various surfaces, such as skin or flooring tile.

It is believed that cleansers and cleansing products manufactured by the previous methods of the present invention permit varying the cleanser by loading different solvents than commercially available liposome cleaners, and thus may be used in a variety of environments, such as the paint and printing industries. Furthermore, the higher solvent loading as demonstrated in the previous examples allows the loaded solvent to cleanse soiled surfaces, as opposed to relying on the liposome for the cleansing action. Relying on the liposome may require the liposome to breakdown and reform to capture dirt or soil, and thereafter be removed by a freed solvent. In the present desired embodiments, the liposomes, as an example the NOVASOME™ PLVs, may be left behind after washing for moisturizing the skin, thereby replacing natural oils removed during the cleaning process. This moisturizing effect may permit the use of solvents that remove natural oils and dry the skin because the NOVASOME™ PLVs left behind replenish the lost oils.

Tests were conducted utilizing cleansing products of the present invention and a commercially available cleansing product. Vinyl flooring tiles were soiled and then a cleansing product was applied. After cleaning, the soil removal percent was calculated by comparing measurements taken prior to and after soiling.

The equipment used included a GARDNER ABRASION TESTER™ apparatus manufactured by BYK Gardner of Riverspark, Ill. 60466 and a CR-310 CHROMA METER™ reflectometer manufactured by Minolta of 101 Williams Drive, Ramsey, N.J. 07446. Furthermore, the tiles used were vinyl flooring tiles manufactured by Armstrong World Industries of Lancaster, Pa. 17604. Also, towels were used during the cleaning of the tiles. These towels are sold under the trade designation WORKHORSE™ Rag Number 41200, manufactured by Kimberly-Clark Corporation, of 200 Bay Bridge Road, Mobile, Ala. 36610.

In addition, several soils were used. These soils included a oil based printers ink, a modified gear grease, and a fiberless roofing tar. The modified gear grease included 96 weight percent wheel bearing grease sold as PENNZOIL PREMIUM™ wheel bearing grease manufactured by Pennzoil Company, P.O. Box 2967, Houston, Tex. 77252-6040. Carbon black of an amount of 4 weight percent was added to the gear grease to serve as an indicator. Moreover, several soil diluents were used. An isoparaffin diluent sold under the trade designation ISOPAR K, H, or M, manufactured by Exxon Chemical Company of P.O. Box 3272, Houston, Tex. 77253-3272 was used with the modified gear grease and an odorless mineral spirit was used to diluent the ink and tar.

The tested cleansing products of the present invention included a cleanser mixed with carriers as previously described. The three cleansers included about a 60 weight percent d-limonene loaded NOVASOME™ PLVs, about a 60 weight percent dibasic ester loaded NOVASOME™ PLVs, and about a 60 weight percent of d-limonene and dibasic ester loaded NOVASOME™ PLVs. The solvent of the d-limonene and dibasic ester loaded NOVASOME™ PLVs is a mixture of approximately 50 percent d-limonene and approximately 50 percent dibasic ester.

The cleansing products of the present invention were compared with a commercially available cleansing product, namely a SANI-TUFF® extra duty cleanser with scrubbers manufactured by Kimberly-Clark Corporation Sani-Fresh International at 4702 Goldfield, San Antonio, Tex. 78218-4637. The commercially available cleansing product includes EMULSION BLEND™ and INDUSTRIAL BLEND™ carriers, as well as a solvent loaded NOVASOME™ PLVs. The solvent is 10-chain carbon mono-esters of acetic acid, sold under the trade designation EXXATE 1000® by Exxon Chemical of America, P.O. Box 3272, Houston, Tex. 77253-3272.

The test procedure for a trial run included testing each cleansing product with each soil in triplicate on about 30.48 centimeter (hereinafter may be referred to as "cm") by about 7.62 cm rectangular tiles. The tests were conducted on a smooth, finished tile side. Each tile was cleaned with a multipurpose cleaner and allowed to air dry prior to the initial reflectometer measurements.

After standardizing the reflectometer, initial readings were taken and marked using a template. Afterwards, three tiles were soiled for each cleansing product and soil combination. The amounts of soil and diluent placed on each tile are depicted below in Table 1.

TABLE 1

| Tile Side | Soil Type | Amount Used (grams) | Soil Diluents | Amount Used (grams) |
|---|---|---|---|---|
| Finished | Modified Gear Grease | 0.2 | Isopar K, H, or M | 0.2 |
| Finished | Fiberless Roofing Tar | 0.2 | Odorless Mineral Spirits | 0.4 |
| Finished | Oil Based Printers Ink | 0.2 | Odorless Mineral Spirits | 0.4 |

The applied soil was spread evenly in circular strokes across the tile surface, and finished with smooth, even lengthwise strokes. Afterwards, the soil was allow to cure for about 18 hours.

After curing, three reflectometer readings were taken of each tile at the same positions as the initial readings by using the template.

After the readings, the tiles were cleaned in a GARDNER ABRASION TESTER™ apparatus. A rectangular WORKHORSE™ towel having dimensions of about 17 cm by about 34 cm was cut in about half and wrapped around a wooden block with its smooth side facing the block. Two grams of a cleansing product was applied to the towel for each test and the block was mounted in the tester. Each soiled tile was clamped into a pan facing the block. The tester was run for 50 cycles. After 50 cycles, the towel was removed and about half of a clean towel without cleansing product was wrapped on the block and run for 5 cycles. Afterwards, the tile was removed and three measurements were taken with the reflectometer at the same positions as before using the template.

The percent of soil removal was calculated using the following formula:

$$(Rc-Rs)/(Ri-Rs)*100\%$$

where

Rc=Cleaned Tile Reflectance

Rs=Soiled Tile Reflectance

Ri=Initial Tile Reflectance

Three readings were taken on each tile, and each soil and cleansing product combination was applied to three tiles. Thus, nine readings were taken for each soil and cleansing product combination. The mean of the nine readings was reported for each cleansing product and soil combination, thus completing the data compiling for the first trial run. Afterwards, a second trial run was completed and the data compiled using the same procedure as described above to confirm the first trial run data. The readings from the first and second trial runs were averaged to compare the percent cleaning of each cleansing product.

Table 2 depicts the cleaning percent and respective standard deviation of four cleansing products for removing an oil based printers ink.

TABLE 2

| Cleansing Product | Average Cleaning Percent | Standard Deviation Percent |
|---|---|---|
| Extra Duty with Scrubbers | 42.42 | 6.32 |
| Extra Duty with d-limonene | 19.49 | 4.19 |
| Extra Duty with dibasic esters | 71.17 | 5.18 |
| Extra Duty with d-limonene and dibasic esters | 51.25 | 7.26 |

Figure 5:
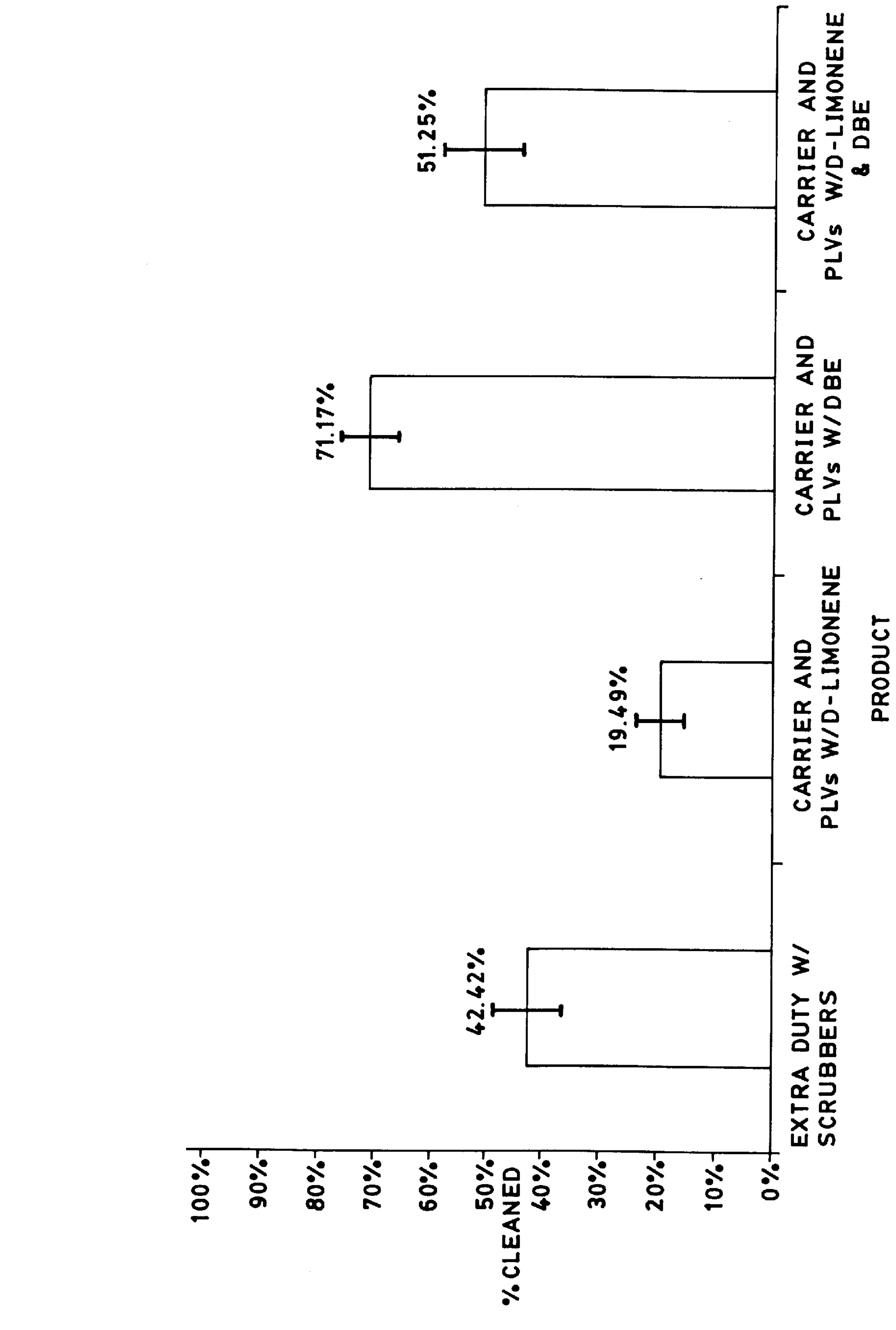
FIG. 5 compares the percent cleaning for one soil type of three exemplary cleansing product embodiments of the present invention and one commercially available cleansing product.

FIG. 5 depicts the data in Table 2. As illustrated in FIG. 5, the dibasic ester solvent cleansing product is particularly well-suited for removing inks, as demonstrated by it having almost twice the cleaning percent as compared to the commercially available cleansing product. These inks are often present in the paint and printing industry.

Table 3 depicts cleaning percent of four cleansing products for removing a fiberless roofing tar.

TABLE 3

| Cleansing Product | Average Cleaning Percent | Standard Deviation Percent |
|---|---|---|
| Extra Duty with Scrubbers | 67.60 | 5.35 |
| Extra Duty with d-limonene | 79.61 | 1.96 |
| Extra Duty with dibasic esters | 62.22 | 10.76 |
| Extra Duty with d-limonene and dibasic esters | 73.65 | 5.98 |

Figure 6:
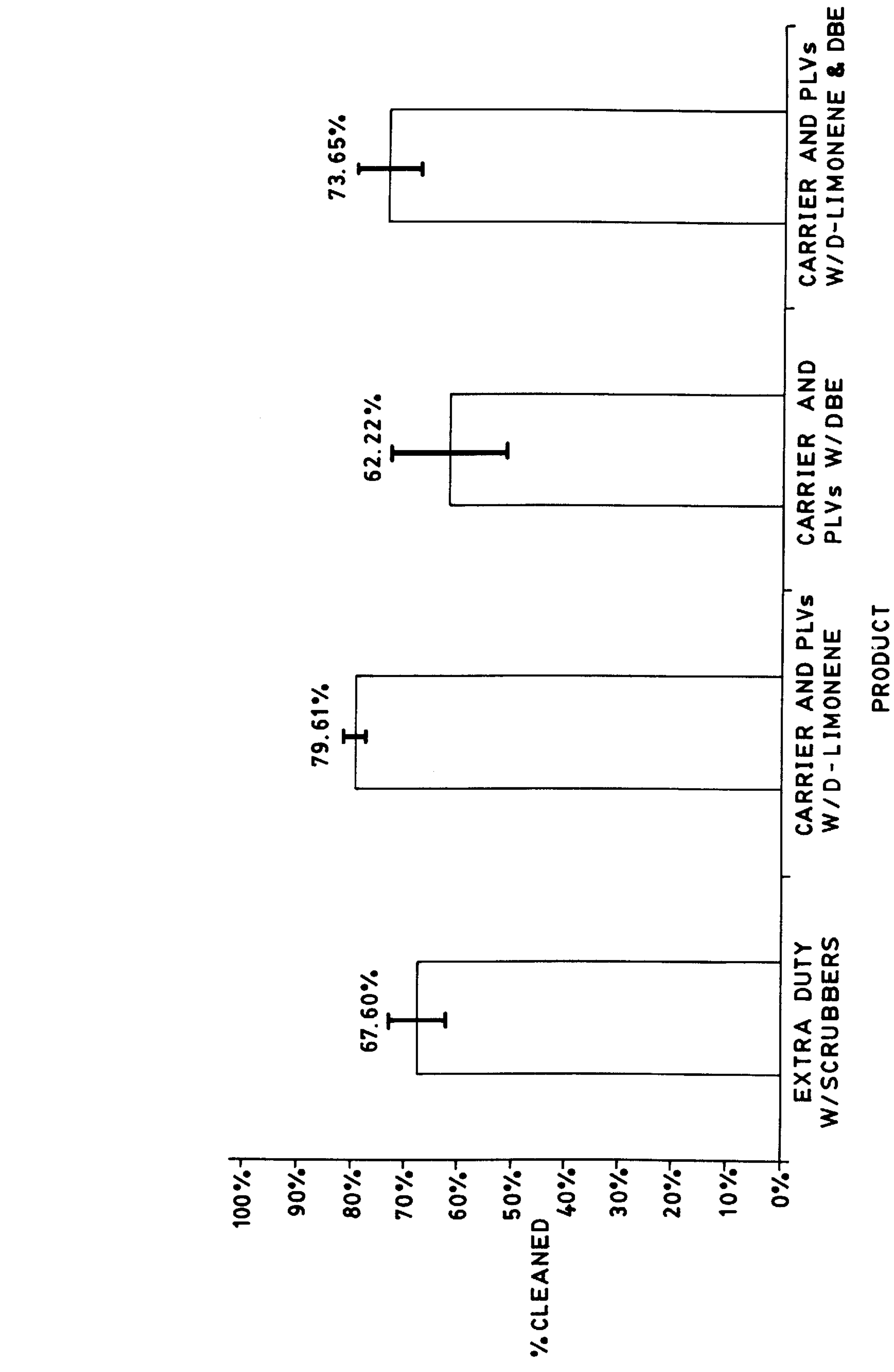
FIG. 6 compares the percent cleaning for a second soil type of three exemplary cleansing product embodiments of the present invention and one commercially available cleansing product.

FIG. 6 depicts the data in Table 3. As illustrated in FIG. 6, the d-limonene solvent cleansing product for removing tar slightly improves the cleaning percent as compared to the commercially available cleansing product. FIGS. 5 and 6 in combination demonstrate the flexibility of the present invention by permitting the loading of various solvents into the liposome cleansing products for removing various soils.

Table 4 depicts cleaning percent of four cleansing products for removing a modified gear grease.

TABLE 4

| Cleansing Product | Average Cleaning Percent | Standard Deviation Percent |
|---|---|---|
| Extra Duty with Scrubbers | 70.75 | 2.63 |
| Extra Duty with d-limonene | 72.92 | 2.29 |
| Extra Duty with dibasic esters | 72.53 | 1.52 |
| Extra Duty with d-limonene and dibasic esters | 63.88 | 2.78 |

Figure 7:
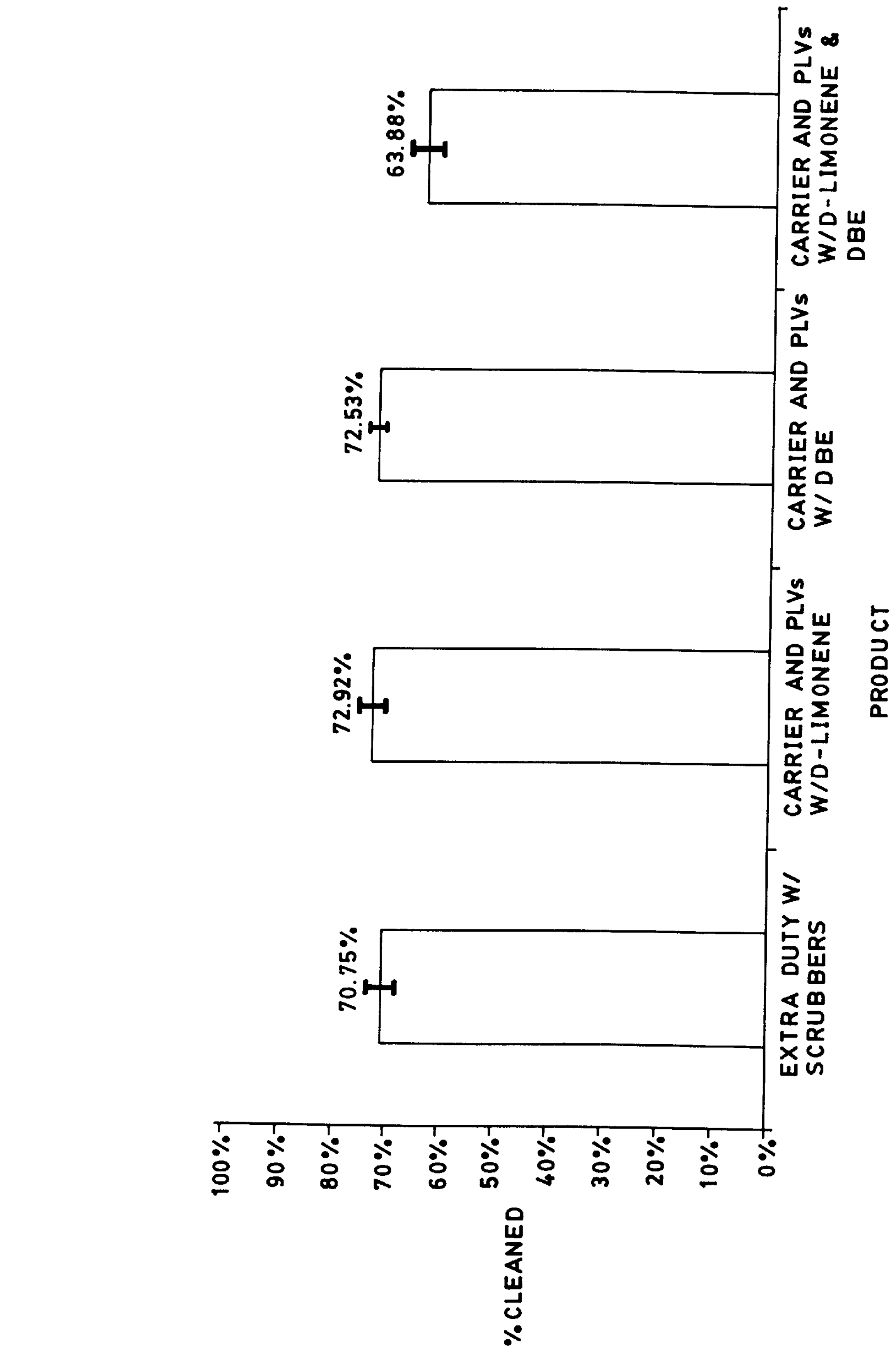
FIG. 7 compares the percent cleaning for a third soil type of three exemplary cleansing product embodiments of the present invention and one commercially available cleansing product.

FIG. 7 depicts the data in Table 4. As illustrated in FIG. 7, the various solvent-loaded cleansing products of the present invention provide about the same percent cleaning as commercially available liposome cleansing products, but still illustrate the flexibility of the present invention for cleaning various soils.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method of cleansing a soiled surface, said method comprising the steps of:

(a) applying a cleanser to said soiled surface, said cleanser comprising a liposome and greater than about 40 weight percent of a solvent chosen from the group consisting of terpenes, dibasic esters, isoprenoids, and mixtures thereof;

(b) rubbing said cleanser against said soiled surface; and (c) removing said cleanser from said soiled surface to provide a cleansed surface.

2. The method of claim 1 wherein said cleanser is formed by loading said liposome with said solvent more than about 7 days after the manufacture of said liposome.

3. The method of claim 1 wherein said solvent in said cleanser is d-limonene.

4. The method of claim 1 wherein said solvent in said cleanser is a dibasic acid ester.

5. The method of claim 1 wherein said liposome in said cleanser is selected from the group consisting of large unilamellar vesicles, multilamellar vesicles, paucilamellar vesicles, and small unilamellar vesicles.

6. The method of claim 5 wherein said liposome in said cleanser is a paucilamellar vesicle.

7. The method of claim 1 wherein the weight percent of said solvent in said cleanser is greater than about 60 percent.

8. The method of claim 7 wherein the weight percent of said solvent in said cleanser is greater than about 80 percent.

9. The method of claim 1 wherein the solvent in said cleanser comprises d-limonene and a dibasic ester in a 1:1 weight ratio.

10. A method of cleansing a soiled surface, said method comprising the steps of:

(a) applying a cleanser to said soiled surface, said cleanser comprising a paucilamellar vesicle and greater than about 40 weight percent of a dibasic ester solvent, wherein said solvent has been loaded into said paucilamellar vesicle more than about 90 days after the manufacture of said paucilamellar vesicle;

(b) rubbing said cleanser against said soiled surface; and (c) removing said cleanser from said soiled surface to provide a cleansed surface.

* * * * *